(12) United States Patent
Ozkan

(10) Patent No.: US 9,982,471 B2
(45) Date of Patent: May 29, 2018

(54) METHODS, SYSTEMS, AND PRODUCTS FOR DETECTION OF ENVIRONMENTAL CONDITIONS

(71) Applicant: AT&T Intellectual Property I, L.P., Atlanta, GA (US)

(72) Inventor: Mehmet Ozkan, Allen, TX (US)

(73) Assignee: AT&T INTELLECTUAL PROPERTY I, L.P., Atlanta, GA (US)

( * ) Notice: Subject to any disclaimer, the term of this patent is extended or adjusted under 35 U.S.C. 154(b) by 0 days. days.

(21) Appl. No.: 15/399,908

(22) Filed: Jan. 6, 2017

(65) Prior Publication Data

US 2017/0114585 A1 Apr. 27, 2017

Related U.S. Application Data

(63) Continuation of application No. 14/466,130, filed on Aug. 22, 2014, now Pat. No. 9,556,812.

(51) Int. Cl.
| | |
|---|---|
| *F02D 41/04* | (2006.01) |
| *E05F 15/72* | (2015.01) |
| *G01N 33/00* | (2006.01) |
| *G05B 9/02* | (2006.01) |
| *F02D 41/26* | (2006.01) |

(52) U.S. Cl.
CPC ............ *E05F 15/72* (2015.01); *F02D 41/042* (2013.01); *F02D 41/26* (2013.01); *G01N 33/004* (2013.01); *G01N 33/0063* (2013.01); *G05B 9/02* (2013.01); *E05Y 2800/42* (2013.01); *F02D 2200/70* (2013.01)

(58) Field of Classification Search
CPC ........ E05F 15/72; F02D 41/26; F02D 41/042; F02D 2200/70; G01N 33/0063; G01N 33/004; G05B 9/02; E05Y 2800/42
See application file for complete search history.

(56) References Cited

U.S. PATENT DOCUMENTS

| | | | | |
|---|---|---|---|---|
| 4,338,526 | A | * 7/1982 | Martin ................... | E05F 15/72 307/116 |
| 4,360,801 | A | * 11/1982 | Duhame .............. | G08B 17/117 318/16 |
| 4,433,274 | A | * 2/1984 | Duhame .............. | G08B 17/117 318/16 |
| 4,464,651 | A | * 8/1984 | Duhame .............. | G08B 17/117 318/16 |

(Continued)

FOREIGN PATENT DOCUMENTS

CA 2258884 A1 7/2000

OTHER PUBLICATIONS

Lee, Arthur, "Demonstration of a Remote Carbon Monoxide Sensing Automatic Shut Off Device for Portable Generators", Aug. 2006, 43 pages.

*Primary Examiner* — Joseph Dallo
(74) *Attorney, Agent, or Firm* — Scott P. Zimmerman, PLLC

(57) ABSTRACT

Methods, systems, and products monitor environmental conditions in an enclosed environment, such as a garage or storage shed. If a dangerous environmental condition is determined, such as elevated carbon monoxide, an entry door may be opened. If further remedial measures are required, ignition of an internal combustion engine may be prohibited.

20 Claims, 23 Drawing Sheets

(56) References Cited

U.S. PATENT DOCUMENTS

| | | | |
|---|---|---|---|
| 4,847,542 A * | 7/1989 | Clark | G07C 9/00182 |
| | | | 318/467 |
| 4,929,877 A * | 5/1990 | Clark | G07C 9/00182 |
| | | | 318/467 |
| 5,333,703 A | 8/1994 | James et al. | |
| 5,576,739 A | 11/1996 | Murphy | |
| 6,040,636 A | 3/2000 | DiCroce | |
| 6,983,726 B1 | 1/2006 | Luo et al. | |
| 7,183,933 B2 * | 2/2007 | Dzurko | G08B 21/14 |
| | | | 318/280 |
| 7,228,213 B2 | 6/2007 | Sakai et al. | |
| 7,342,368 B2 | 3/2008 | Roman | |
| 7,710,284 B2 * | 5/2010 | Dzurko | G08B 21/16 |
| | | | 340/632 |
| 8,375,913 B2 | 2/2013 | Kwiecinski et al. | |
| 8,519,836 B2 | 8/2013 | Grossman | |
| 8,643,467 B2 | 2/2014 | Chutorash et al. | |
| 8,669,878 B1 * | 3/2014 | Vantilburg | A62B 5/00 |
| | | | 318/282 |
| 9,053,626 B2 * | 6/2015 | Cristoforo | G08B 21/14 |
| 2003/0117728 A1 | 6/2003 | Hutzel | |
| 2005/0212681 A1 | 9/2005 | Dzurko | |
| 2006/0202815 A1 | 9/2006 | John | |
| 2007/0146150 A1 | 6/2007 | Calabrese | |
| 2007/0182574 A1 | 8/2007 | Dzurko | |
| 2007/0247096 A1 * | 10/2007 | Tang | E05F 15/70 |
| | | | 318/280 |
| 2008/0280551 A1 | 11/2008 | Ashworth | |
| 2008/0284579 A1 * | 11/2008 | Contreras | G07C 9/00182 |
| | | | 340/501 |
| 2009/0146846 A1 | 6/2009 | Grossman | |
| 2010/0171588 A1 | 7/2010 | Chutorash | |
| 2010/0201531 A1 | 8/2010 | Pakravan | |
| 2010/0225493 A1 | 9/2010 | Zishaan | |
| 2011/0030639 A1 * | 2/2011 | Kwiecinski | F02N 11/0807 |
| | | | 123/179.2 |
| 2011/0032115 A1 * | 2/2011 | Kwiecinski | F02N 11/0807 |
| | | | 340/12.22 |
| 2011/0063101 A1 * | 3/2011 | Cristoforo | G08B 21/14 |
| | | | 340/501 |
| 2011/0204720 A1 | 8/2011 | Ruis | |
| 2011/0241877 A1 | 10/2011 | Wedig | |
| 2012/0208519 A1 | 8/2012 | Seaver | |
| 2012/0260575 A1 | 10/2012 | Monaco | |
| 2012/0310547 A1 | 12/2012 | Cristoforo | |
| 2014/0074383 A1 | 3/2014 | Frey | |
| 2017/0193789 A1 * | 7/2017 | Economy | G08B 21/14 |

* cited by examiner

METHODS, SYSTEMS, AND PRODUCTS FOR DETECTION OF ENVIRONMENTAL CONDITIONS

CROSS-REFERENCE TO RELATED APPLICATION

This application is a continuation of U.S. application Ser. No. 14/466,130 filed Aug. 26, 2014 and since issued as U.S. Pat. No. 9,556,812, and incorporated herein by reference in its entirety.

BACKGROUND

Harmful exposure to noxious gases is well documented. For example, the ill effects of carbon monoxide are well known, yet hundreds of people are poisoned every year by operating a vehicle in a closed garage.

BRIEF DESCRIPTION OF THE SEVERAL VIEWS OF THE DRAWINGS

The features, aspects, and advantages of the exemplary embodiments are better understood when the following Detailed Description is read with reference to the accompanying drawings, wherein.

DETAILED DESCRIPTION

The exemplary embodiments will now be described more fully hereinafter with reference to the accompanying drawings. The exemplary embodiments may, however, be embodied in many different forms and should not be construed as limited to the embodiments set forth herein. These embodiments are provided so that this disclosure will be thorough and complete and will fully convey the exemplary embodiments to those of ordinary skill in the art. Moreover, all statements herein reciting embodiments, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure).

Thus, for example, it will be appreciated by those of ordinary skill in the art that the diagrams, schematics, illustrations, and the like represent conceptual views or processes illustrating the exemplary embodiments. The functions of the various elements shown in the figures may be provided through the use of dedicated hardware as well as hardware capable of executing associated software. Those of ordinary skill in the art further understand that the exemplary hardware, software, processes, methods, and/or operating systems described herein are for illustrative purposes and, thus, are not intended to be limited to any particular named manufacturer.

As used herein, the singular forms "a," "an," and "the" are intended to include the plural forms as well, unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

It will also be understood that, although the terms first, second, etc. may be used herein to describe various elements, these elements should not be limited by these terms. These terms are only used to distinguish one element from another. For example, a first device could be termed a second device, and, similarly, a second device could be termed a first device without departing from the teachings of the disclosure.

Figure 1:
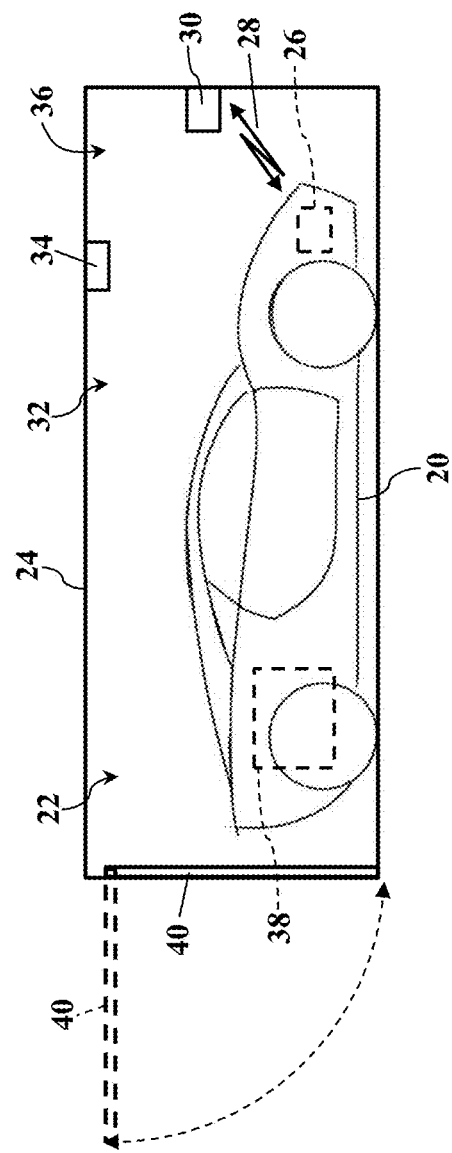
FIG. 1 is a simplified schematic illustrating an environment in which exemplary embodiments may be implemented.

FIG. 1 is a simplified schematic illustrating an environment in which exemplary embodiments may be implemented. FIG. 1 illustrates a vehicle 20 parked in a closed environment 22, such as a garage 24 or other storage location. The vehicle 20 has a transceiver 26 that receives a signal 28 sent from an environmental monitor 30. The signal 28 contains information describing the environmental conditions 32 within the closed environment 22. The environmental monitor 30, for example, may interface with one or more environmental sensors 34 to determine the level of carbon monoxide (CO) 36 within the garage 24. As most readers understand, if the vehicle's engine 38 runs while parked in the garage 24, dangerous levels of carbon monoxide 36 may develop. The signal 28 may thus indicate the level of carbon monoxide 36 within the garage 24, as determined by the environmental monitor 30. Exemplary embodiments may thus open a garage door 40 to reduce the carbon monoxide 36 within the garage 24. Indeed, should the level of carbon monoxide 36 become dangerous, exemplary embodiments may even stop ignition and/or fuel to the engine 38, thus ceasing production of harmful carbon monoxide 36. Exemplary embodiments may implement other actions based on any other environmental condition 32, as later paragraphs explain.

Figure 2:
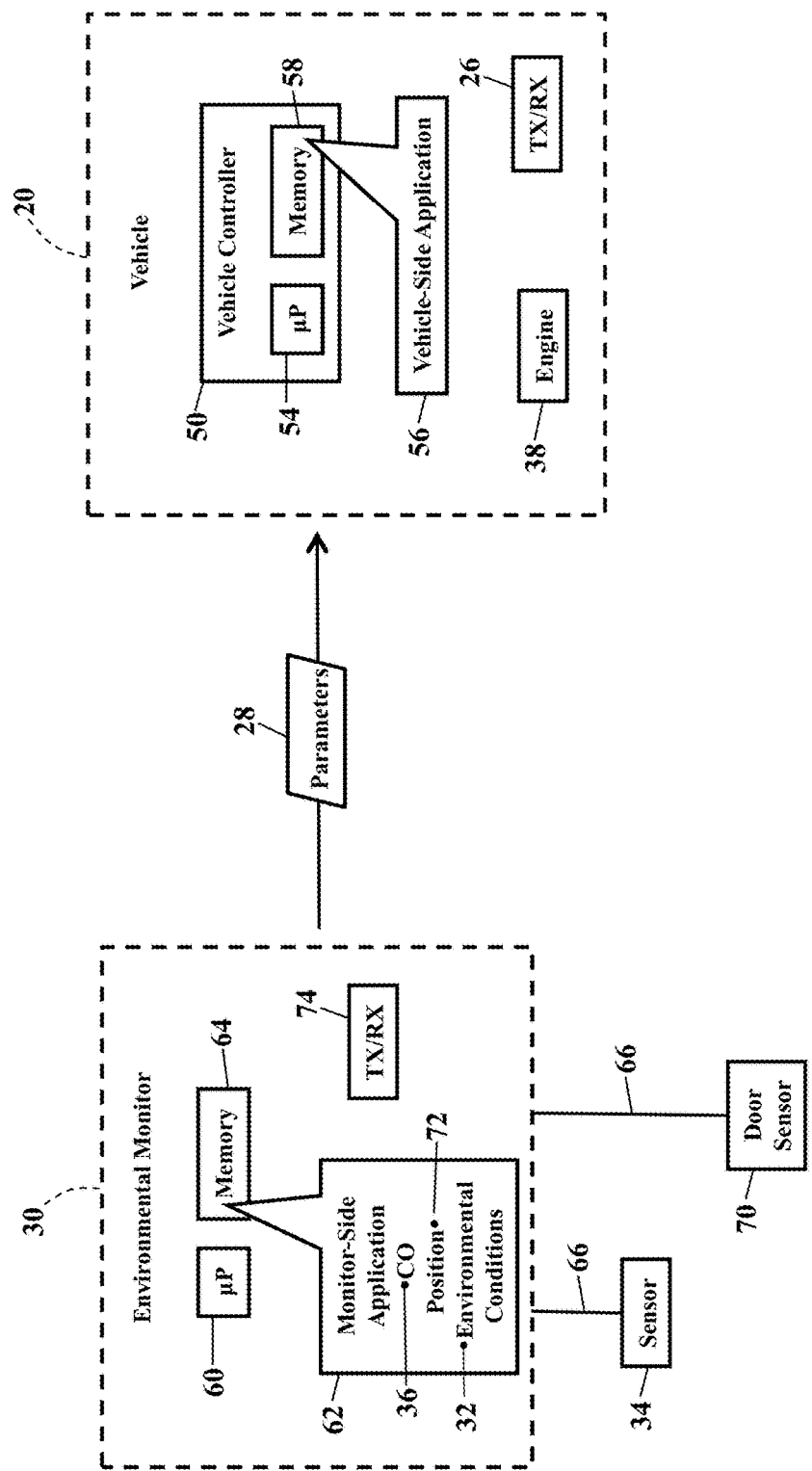
FIGS. 2-4 are more detailed block diagrams illustrating the operating environment, according to exemplary embodiments.
Figure 3:
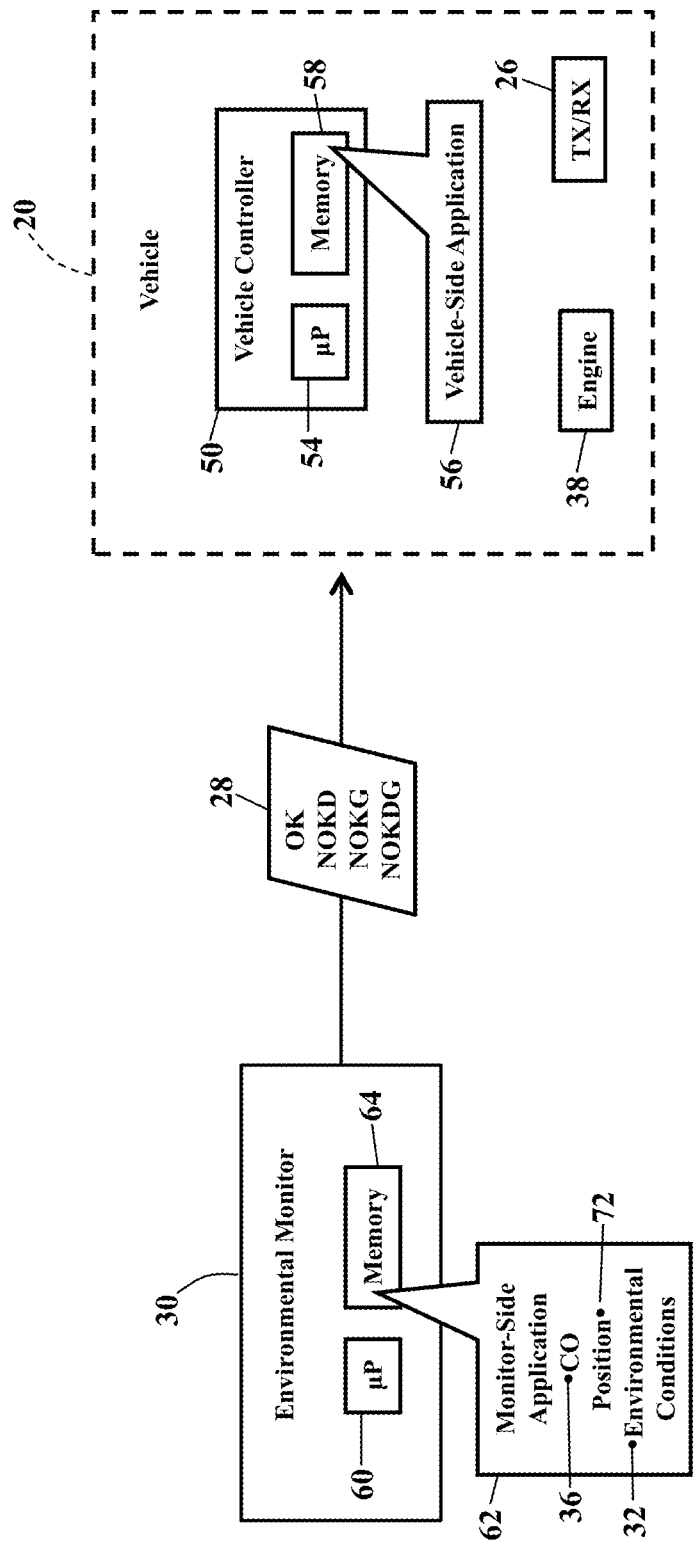
Figure 4:
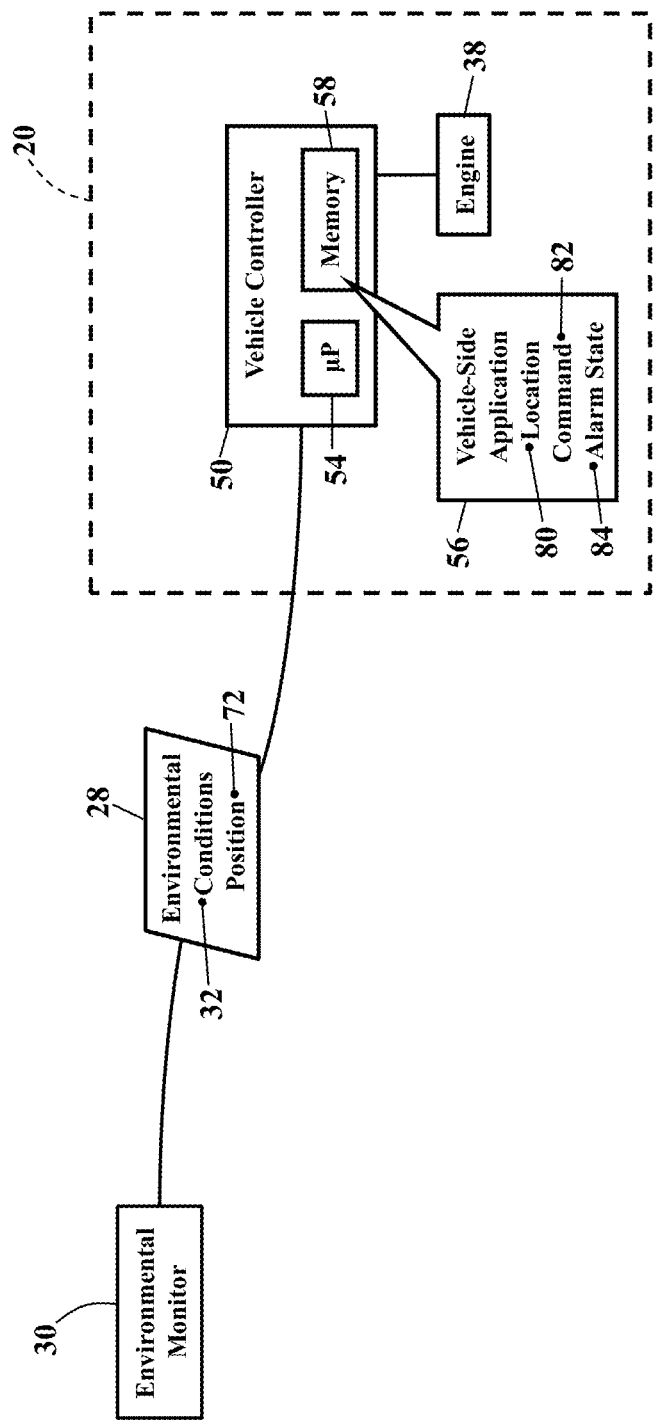

FIGS. 2-4 are more detailed block diagrams illustrating the operating environment, according to exemplary embodiments. Here the vehicle 20 has at least one vehicle controller 50 that interfaces with the vehicle transceiver 26 (illustrated as "TX/RX"). The vehicle controller 50 has a processor 54 (e.g., "µP"), application specific integrated circuit (ASIC), or other component that executes a vehicle-side application 56 stored in a memory 58. The vehicle-side application 56 is a set of programming, code, or instructions that instruct the processor 54 to perform operations. The processor 54, for example, instructs the vehicle transceiver 26 to receive the signal 28 sent from the environmental monitor 30. As the vehicle 20 may be a so-called "smart" or "connected" car or truck, the vehicle-side application 56 may be downloaded using a communications network (such as WI-FI® or cellular). The vehicle-side application 56 may thus be a module or "app" that is downloaded to the vehicle 20. However, the vehicle 20 may also interface with a mobile device to receive the signal 28 sent from the environmental monitor 30, as FIG. 21 later explains.

The environmental monitor 30 may also be processor controlled. As FIG. 2 also illustrates, the environmental monitor 30 has a processor 60 (e.g., "µP"), application specific integrated circuit (ASIC), or other component that executes a monitor-side application 62 stored in a memory 64. The monitor-side application 62 is a set of programming, code, or instructions that instruct the processor 60 to perform operations. The processor 60, for example, obtains one or more output signals 66 generated by the environmental sensor(s) 34. Because there are many known interfaces to many different sensors, no detailed explanation is needed, for any interface is applicable. For simplicity, the output signal 66 may represent the level of carbon monoxide 36 within the garage (illustrated as reference numeral 24 in FIG. 1). Later paragraphs will describe other sensory factors.

The environmental monitor 30 may also interface with other sensors. For example, the processor 60 may obtain the output signal 66 generated by a door sensor 70. The door sensor 70 produces the output signal 66 indicating a position 72 of the garage door 40. The door sensor 70 may sense whether the garage door 40 is in a fully opened position or in a fully closed position. The door sensor 70 may sense any other position 72, such as partially open at ¼, ½, or ¾ positions from fully open or closed. Because there are many known door and/or position sensors, no detailed explanation is needed.

The environmental monitor 30 sends the signal 28. Once the output signal(s) 66 is/are received, the processor 60 generates the signal 28 having parameters that describe the environmental conditions 32 within the closed environment (illustrated as reference numeral 22 in FIG. 1). Again, for simplicity, the signal 28 may represent the level of carbon monoxide 36 within the garage 24. Because the processor 60 may also interface with the door sensor 70, the signal 28 may additionally or alternatively include another parameter or value that indicates the position 72 of the garage door 40. The environmental monitor 30 may wirelessly broadcast the signal 28 from a transceiver 74.

FIG. 3 further illustrates the signal 28. The transceiver 26 in the vehicle 20 receives the signal 28 transmitted from the environmental monitor 30. The processor 54 in the vehicle controller 50 interfaces with the transceiver 26 to obtain the informational content in the signal 28. As FIG. 3 illustrates, the signal 28 may have different values or informational content, depending on the environmental conditions 32 (within the closed environment 22) and/or the position 72 of the garage door (illustrated as reference numeral 40 in FIG. 1). An "OK" signal 28, for example, may indicate that the garage door 40 is "open" and there is no CO alarm in the environment. A "NOKD" (or "Not OK Door") may indicate that garage door 40 "closed" (or "not open"). The "NOKG" (or "Not OK Gas") signal 28 may indicate that the environmental monitor 30 has determined a CO gas alarm in the environment. The "NOKDG" (or "Not OK Door & Gas") may indicate that the garage door is "closed" and there is a critical CO alarm in the environment.

As FIG. 4 illustrates, the vehicle controller 50 processes the signal 28. The signal 28 transmitted from the environmental monitor 30 may indicate the environmental conditions 32 and/or the position 72 of the garage door 40. The processor 54 in the vehicle controller 50 may then perform operations, based on the signal 28. For example, the vehicle controller 50 may determine a location 80 of the vehicle 20. If the vehicle 20 is parked inside the garage 24 (as FIG. 1 illustrates), and the signal 28 is "OK," then the vehicle controller 50 may permit ignition and fuel, thus permitting the internal combustion engine 38 to operate. That is, even though the vehicle 20 is parked inside the garage 24, no elevated carbon monoxide is detected, so the engine 38 may be started.

Exemplary embodiments may continuously monitor for environmental concerns. The vehicle-side application 56 may be initiated as soon as an ignition key is inserted or an ignition switch is depressed. That is, the processor 54 may execute the vehicle-side application 56 at any time or moment before and during ignition. Any time the engine 38 is running, exemplary embodiments may survey the signal 28 for the environmental conditions 32 and the position 72 of the garage door 40. The vehicle controller 50 may then perform operations, such as determining the location 80 of the vehicle 20. If the vehicle 20 is located outside the garage 24, then perhaps the engine 38 may operate. However, if the vehicle 20 is located inside the garage 24, then actions may be taken to ensure safe environmental conditions 32.

When the engine 38 is running inside the garage 24, actions are taken. If the position 72 indicates the garage door 40 is "closed," or the CO level exceeds some threshold level, the environmental monitor 30 changes its signal 28 to "NOKD," "NOKG," or "NOKGD" (as above explained). As the vehicle-side application 56 causes the vehicle controller 50 to receive and analyze the signal 28, the processor 54 may issue an engine command 82 to immediately stop ignition and/or fuel to the engine 38, thus halting combustion. The vehicle controller 50 may also enter an alarm state 84 of operation requiring notification (as later paragraphs will explain). Likewise, if the signal 28 is "NOK," the vehicle controller 50 stops the engine 38 and enters the alarm state 84 of operation.

Exemplary embodiments may warn of any dangerous environmental conditions 32. Whenever the environmental monitor 30 detects high or dangerous environmental conditions 32 (from the outputs 66 of the sensors 34, as FIG. 2 illustrates), the environmental monitor 30 may also enter the alarm state 84 of operation. The environmental monitor 30 may generate an audible warning, which is output by a speaker or siren. The environmental monitor 30 may also generate an "OPEN" command that instructs a door opener to open the garage door 40. Even the vehicle 20 may take action to reduce the high or dangerous environmental conditions 32, such as also redundantly generating and transmitting an "OPEN" command to open the garage door 40. The vehicle controller 50 may also activate an audible car alarm or horn, activate the hazard flashers and/or headlights, and display a warning message on a display of an instrument panel.

Figure 5:
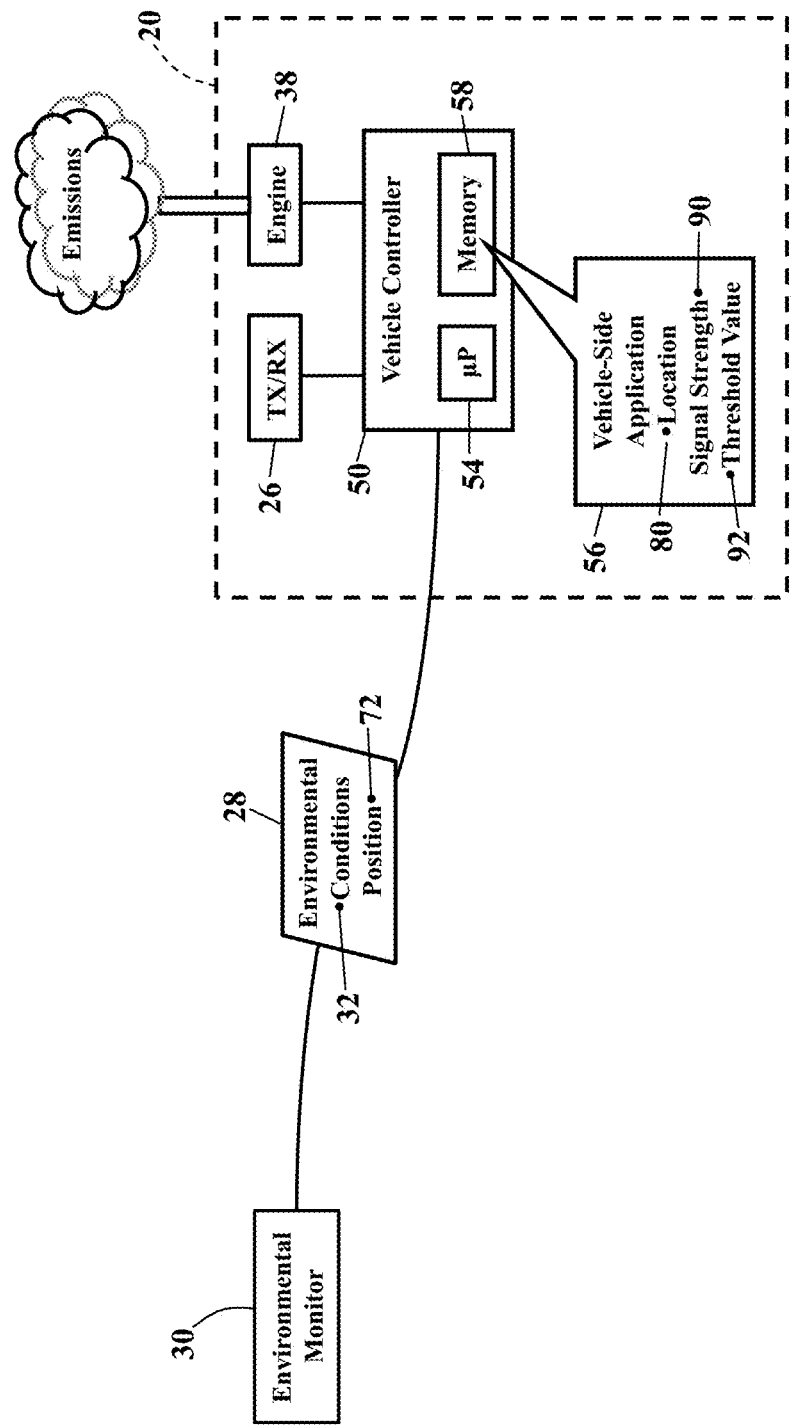
FIG. 5 is a schematic illustrating locational determination of a vehicle, according to exemplary embodiments.

FIG. 5 is a schematic illustrating the locational determination of the vehicle 20, according to exemplary embodiments. As the above paragraphs mention, exemplary embodiments may determine the location 80 of the vehicle 20. The location 80 of the vehicle 20 helps determine whether the engine 38 should combust fuel, producing carbon monoxide and many other emissions. Exemplary embodiments may preferably determine the location 80 of the vehicle 20 based on the signal 28 broadcast from the environmental monitor 30. Whenever the transceiver 26 in the vehicle 20 receives the signal 28, the processor 54 in the vehicle controller 50 may calculate or determine a signal strength 90 of the signal 28. The processor 54 may then compare the signal strength 90 to one or more threshold values 92. The threshold value 92 is selected to correspond with a known location 80 of the vehicle 20. One of the threshold values 92, for example, may be predetermined or calibrated with the signal strength 90 at which the vehicle 20 is fully inside the garage 24. If the signal strength 90 equals or exceeds the threshold value 92, then the vehicle 20 may be assumed parked inside the garage 24. If the signal strength 90 is less than the threshold value 92, then the location 80 of the vehicle 20 may be assumed outside the garage 24.

Figure 6:
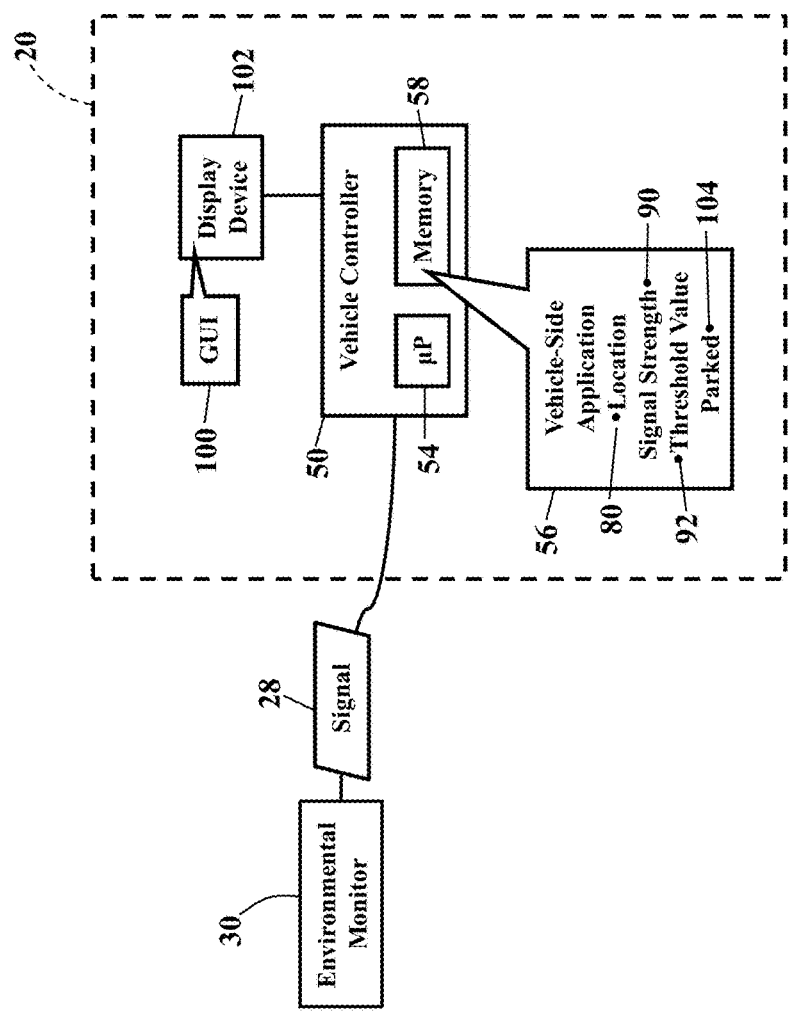
FIGS. 6-7 are schematics further illustrating parking determinations, according to exemplary embodiments.
Figure 7:
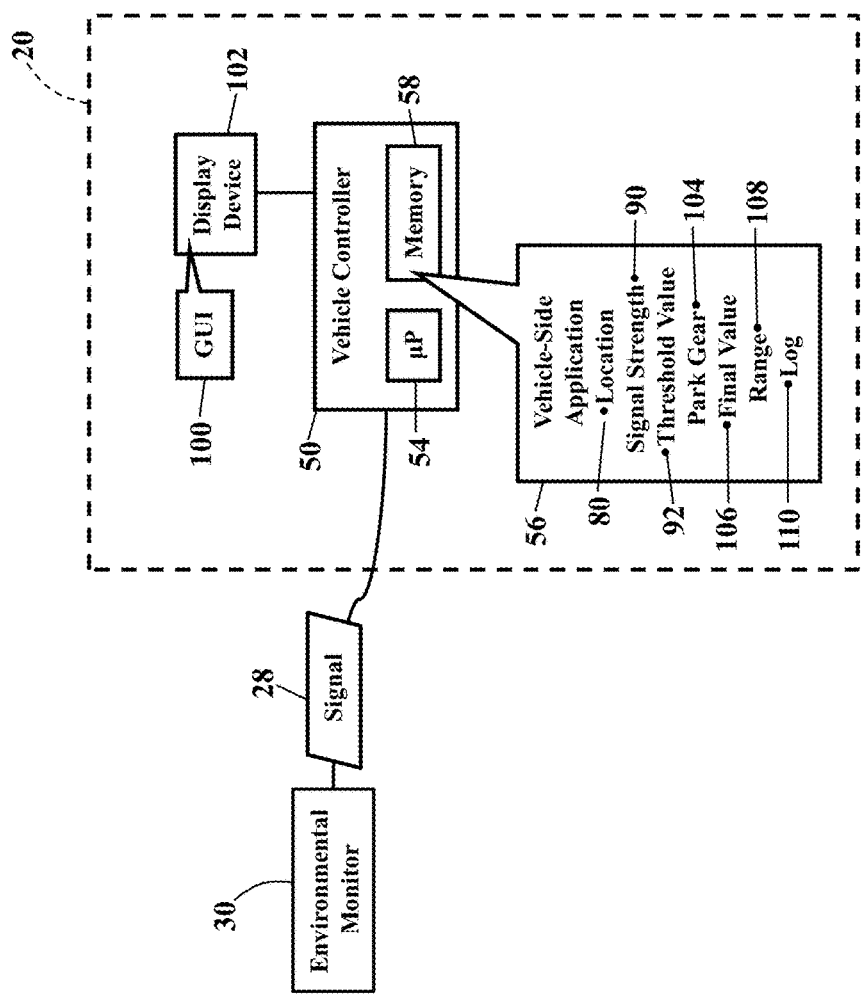

FIGS. 6-7 are schematics further illustrating parking determinations, according to exemplary embodiments. The threshold value 92 may be configured when the vehicle 20 is parked in the garage 24. When a driver parks the vehicle 20 in the garage 24, the driver may manually set the threshold value 92 of the signal strength 90 of the signal 28. The vehicle controller 50 may cause a graphical user interface ("GUI") 100 to be produced on a display device 102. The graphical user interface 100 may have a graphical control or selection for indicating a "parked" location 80 of the vehicle 20. The display device 102 may have a capacitive input touch screen layer, thus allowing the driver's finger to touch and select a "parked" option 104. Selection of the graphical control may cause the vehicle controller 50 to determine the signal strength 90 of the signal 28 in the parked location 80. This signal strength 90, at the parked location 80, is stored as one of the threshold values 92. Any measurement or calculation of the signal strength 90 that is less than the threshold value 92 may indicate the vehicle 20 is located outside the garage 24.

As FIG. 7 illustrates, the threshold value 92 may be based on movement. Most people will install the environmental monitor 30 on a garage wall that faces the vehicle 20. Indeed, a manufacturer or seller may instruct drivers to mount the environmental monitor 30 in a frontal wall position to the vehicle. As the vehicle 20 drives into the garage 24, the vehicle 20 will approach the environmental monitor 30, thus increasing the signal strength 90 of the signal 28 received from the environmental monitor 30. The signal strength 90 may continually increase as the vehicle 20 approaches the environmental monitor 30. At some location 80 the driver will stop forward movement, apply the brakes, and select a "Park" gear position 110 on a transmission. The signal strength 90 of the signal 28 received from the environmental monitor 30 will have reached a final value 106. As most people park in approximately the same location 80 in their garage 24, the final value 106 of the signal strength 90 may be historically observed within some small range 108 of values. That is, the vehicle controller 50 may maintain a log 110 of the final values 106 of the signal strength 90 at which speed is zero (0) and/or the transmission "Park" gear position 110 is selected. As the log 110 grows with entries, the vehicle-side application 56 may cause the processor 56 to calculate a mean value and standard deviation. Whenever the signal strength 90 is within the historical range 108 of values, the vehicle controller 50 may infer that the vehicle 20 is parked in the garage 24.

Exemplary embodiments, however, may use GPS information. As the reader may know, many vehicles have a GPS receiver that determines the current location 80 of the vehicle 20. While exemplary embodiments may use the GPS coordinates to determine when the vehicle 20 is parked in the garage 24, the civilian Global Positioning System may not be accurate enough to confidently raise or lower the garage door 40. The civilian Global Positioning System currently only has an accuracy of about nine (9) meters, and atmospheric conditions may further reduce this accuracy. Moreover, GPS signals are severely attenuated indoors, further degrading reception inside the garage 24. Current GPS technology alone, then, cannot confidently open or close the garage door 40 without risking damage to the vehicle 20.

Figure 8:
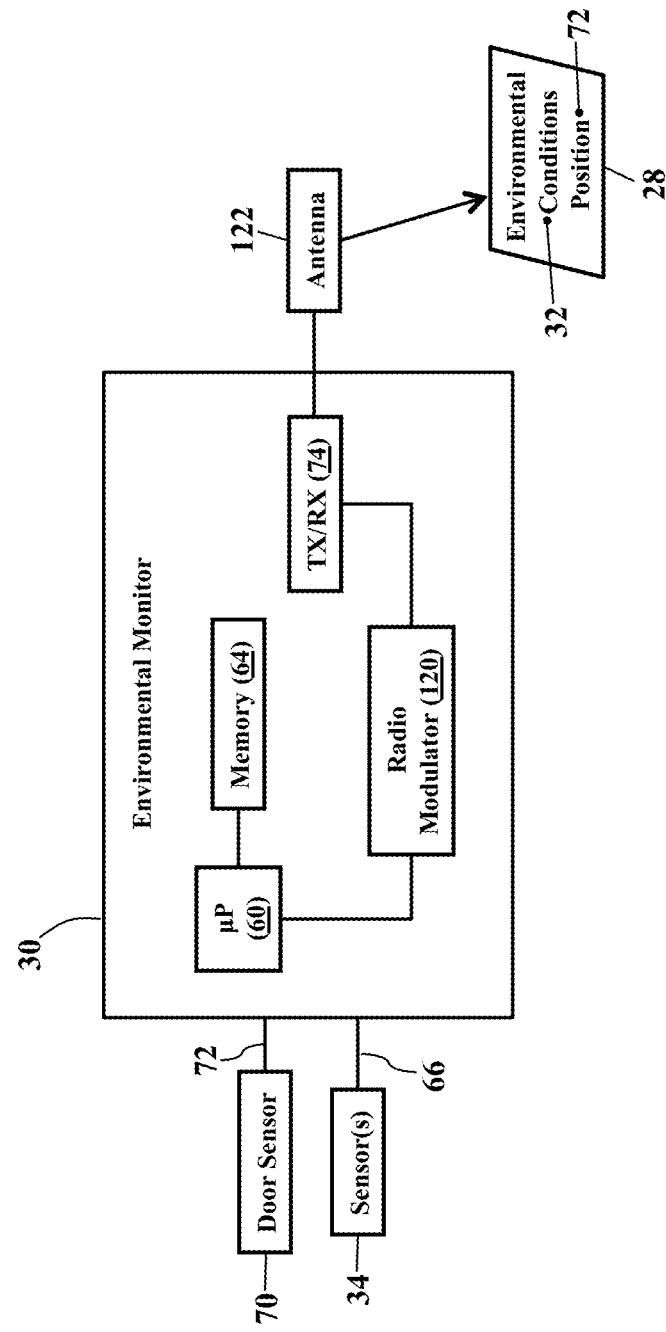
FIGS. 8-9 are more detailed block diagrams of an environmental monitor, according to exemplary embodiments.
Figure 9:
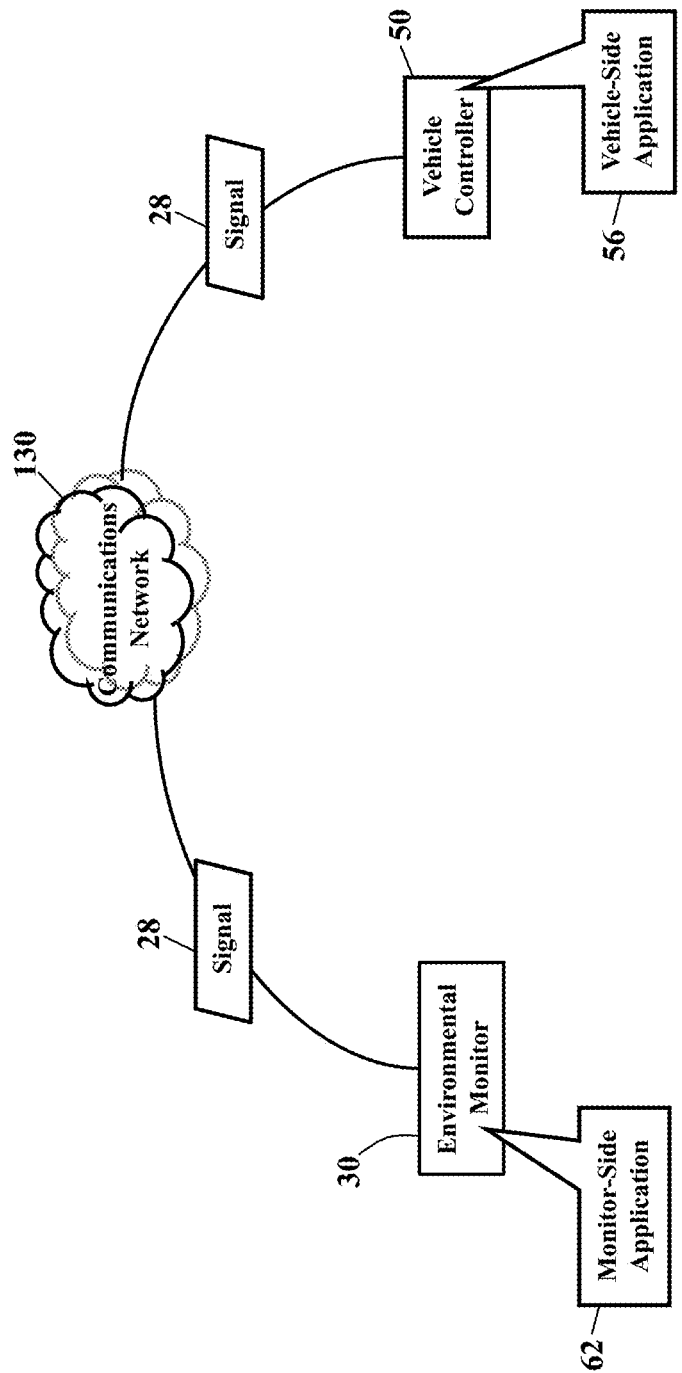

FIGS. 8-9 are more detailed block diagrams of the environmental monitor 30, according to exemplary embodiments. The environmental monitor 30 receives the output signals 66 from the environmental sensors 34. The environmental monitor 30, for example, may have an internal or external CO detector for determining the level of carbon monoxide. The environmental monitor 30 may also interface with the door sensor 70 to receive the position 72 of the garage door 40. The environmental monitor 30 thus analyses the output signals 66 in order to understand the environmental condition(s) and garage door status. The processor 60 instructs a radio signal modulator 120 to create the signal 28 describing the environmental conditions 32 and/or the position 72 of the garage door 40. The processor 60 also instructs the transceiver 74 to transmit the signal 28 using an antenna 122. The environmental monitor 30 may receive electrical power from a battery, an AC power adapter, or renewable energy source. The environmental monitor 30 may thus automatically open the garage door 40 should the CO gas level be critically high and the engine ignition is switched on.

The signal 28 transmitted from the environmental monitor 30 is preferably low energy. Even though the environmental monitor 30 may be AC powered, many users/drivers may not have a nearby AC electrical outlet in their garage. Moreover, should a power outage occur, the environmental monitor 30 may be inoperable. Exemplary embodiments, then, may prefer to utilize battery power for simple, continuous operation. The environmental monitor 30, then, may have low power consumption using BLUETOOTH® LOW ENERGY radio componentry. The environmental monitor 30 may thus broadcast the signal 28 for years using a single, smaller battery. Exemplary embodiments, however, may utilize any portion of the electromagnetic spectrum and any signaling standard.

FIG. 9 illustrates additional networking options. Here the environmental monitor 30 may interface with any communications network 130. The environmental monitor 30, for example, may send messages to, and receive messages from, the vehicle controller 50 using a local area network (such as a WI-FI® network) and/or a wide-area network (such as a cellular network). The environmental monitor 30 may utilize any packetizing protocol (such as any of the Internet protocols) and address packets of data to a network address associated with the vehicle controller 50. Exemplary embodiments, however, may be applied regardless of networking environment. The communications network 130 may utilize any portion of the electromagnetic spectrum and any signaling standard (such as the I.E.E.E. 802 family of standards, GSM/CDMA/TDMA or any cellular standard, and/or the ISM band). The communications network 130 may also utilize a radio-frequency domain and/or an Internet Protocol (IP) domain. The communications network 130, however, may also include a distributed computing network, such as the Internet (sometimes alternatively known as the "World Wide Web"), an intranet, a local-area network (LAN), and/or a wide-area network (WAN). The communications network 130 may also include coaxial cables, copper wires, fiber optic lines, and/or hybrid-coaxial lines. The communications network 130 may even include powerline portions, in which signals are communicated via electrical wiring. The concepts described herein may be applied to any wireless/wireline communications network, regardless of physical componentry, physical configuration, or communications standard(s).

Figure 10:
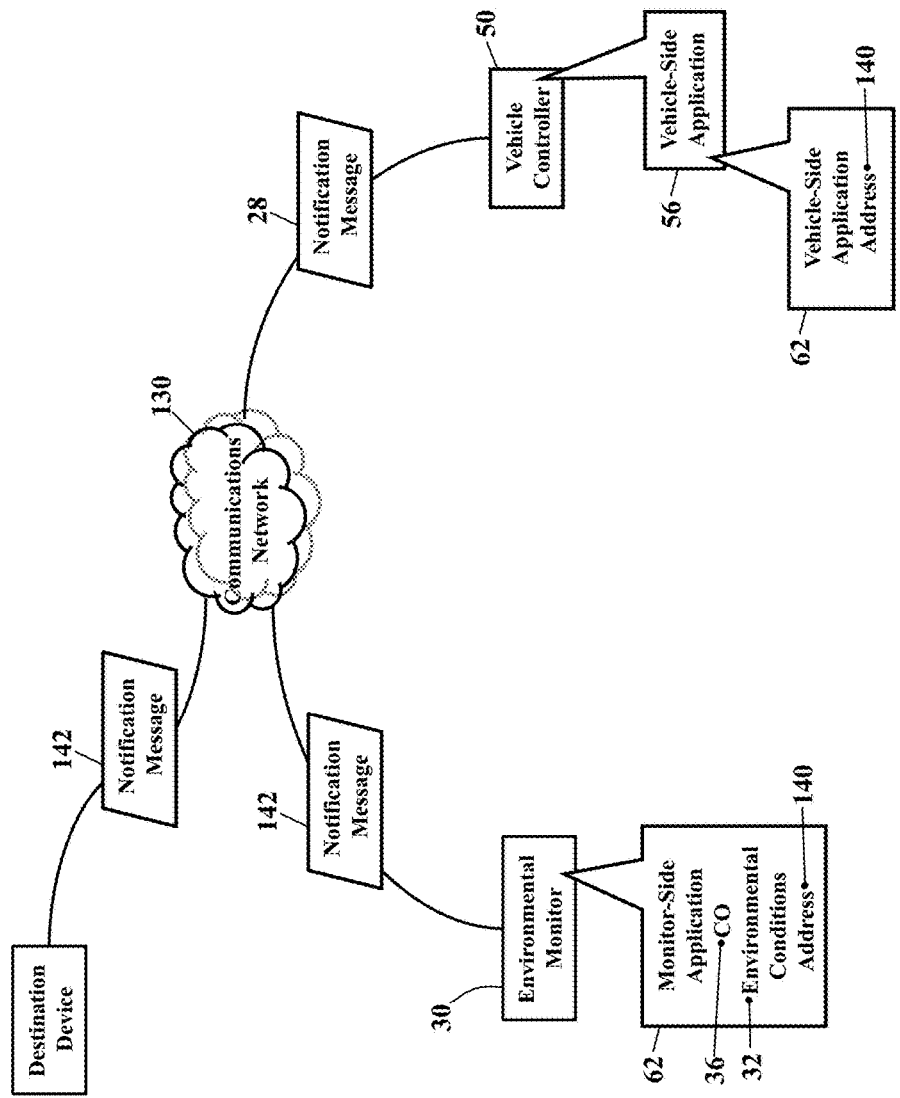
FIGS. 10-11 are schematics illustrating notifications, according to exemplary embodiments.
Figure 11:
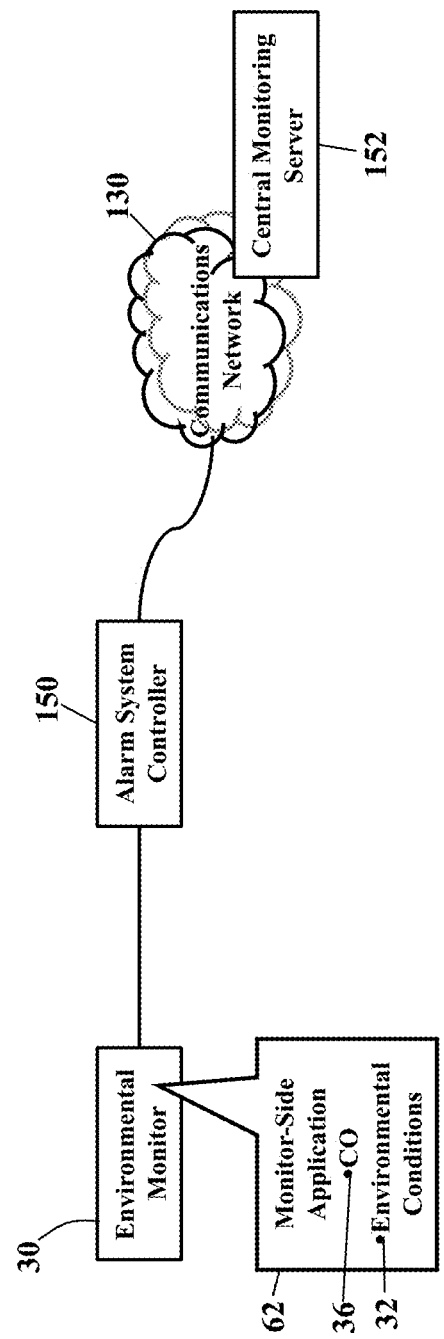

FIGS. 10-11 are schematics illustrating notifications, according to exemplary embodiments. Here exemplary embodiments may notify of hazardous environmental conditions 32 detected by the environmental monitor 30. The environmental monitor 30 may be configured to alert of any particular environmental condition 32, such as an elevated level of carbon monoxide 36. Whenever some threshold environmental condition 32 is determined, the monitor-side application 62 may cause the environmental monitor 30 to retrieve one or more notification addresses 140. The environmental monitor 30 may then generate and send a notification message 142 to each one of the notification addresses 140. The vehicle-side application 56 may also cause the vehicle controller 50 to retrieve the notification addresses 140 and send similar notification messages 142. Each notification message 142 routes into and through the communications network 130 to a destination device associated with the notification address 140. Exemplary embodiments may thus alert friends, family, and emergency personnel to the environmental conditions 32 detected in the garage 24.

FIG. 11 illustrates security notifications. Many homes and businesses may have a security system for protection against intruders and fire. The environmental monitor 30 may thus have an interface to an alarm system controller 150. The environmental monitor 30 may thus continually or periodically inform the alarm system controller 150 to the environmental conditions 32 detected in the garage 24. Whenever a threshold environmental condition 32 is determined, environmental monitor 30 may send a message or command to the alarm system controller 150. The alarm system controller 50 may then contact a central monitoring server 152, thus notifying a central monitoring station. Emergency personnel may thus be summoned, as is generally known.

Figure 12:
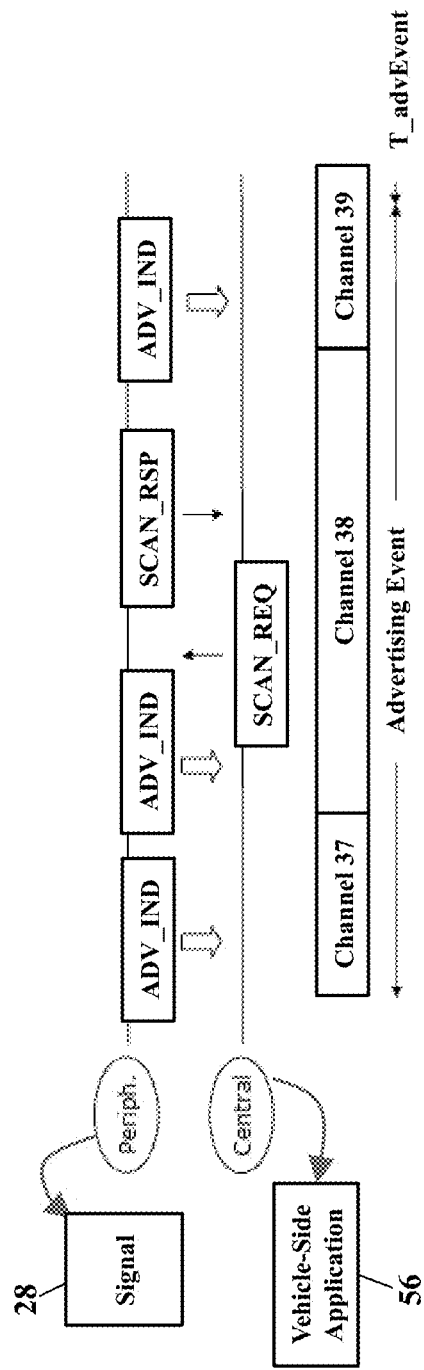
FIGS. 12-13 are schematics illustrating discovery and connection, according to exemplary embodiments.
Figure 13:
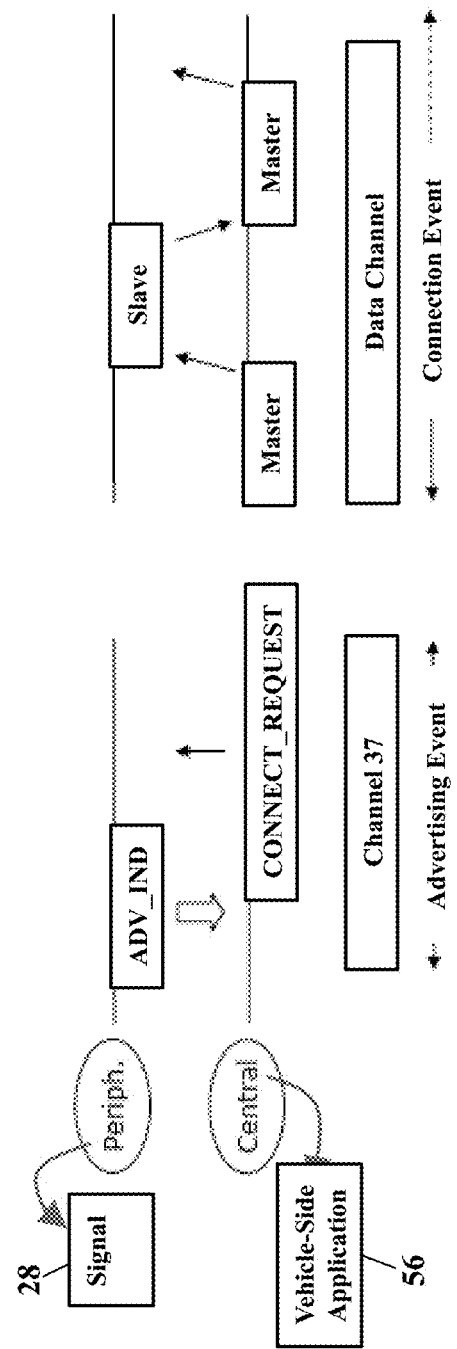

FIGS. 12-13 are schematics illustrating discovery and connection, according to exemplary embodiments. In FIG. 12 the environmental monitor 30 may broadcast, or advertise, itself within the enclosed environment (such as the garage 24, as FIG. 1 illustrates). That is, the environmental monitor 30 may continuously, randomly, or periodically sent its signal 28. The vehicle controller 50 may instruct the transceiver 26 to continuously, randomly, or periodically scan for predefined advertising channels. As the vehicle 20 approaches or enters the garage 24, the vehicle controller 50 detects the transmitted signal 28 within its reach.

FIG. 13 illustrates connection. When the vehicle controller 50 detects the transmitted signal 28, the vehicle-side application 56 causes the vehicle controller 50 to generate a connection request, which is transmitted from the vehicle transceiver 26 using one of the advertising channels. Once a connection is established, the environmental monitor 30 sends the predefined signal 28 (e.g., OK, NOKD, NOKG, or NOKDG) according the environment conditions 32. The vehicle controller 50 detects the network address (e.g., MAC address) in the signal 28 transmitted from the environmental monitor 30. The vehicle controller 50 measures the signal strength 90 (e.g., electromagnetic power) of the transmitted signal 28 and compares to the threshold value(s) 92. The vehicle controller 50 may thus use the signal strength 90 to determine whether the vehicle 20 is inside or outside of the garage 24 (as earlier paragraphs explained). If the signal strength 90 indicates the vehicle 20 is inside the garage 24, the vehicle controller 50 inspects the transmitted signal 28 and executes the predefined operations (such as stopping the engine 38 under alarm conditions).

Figure 14:
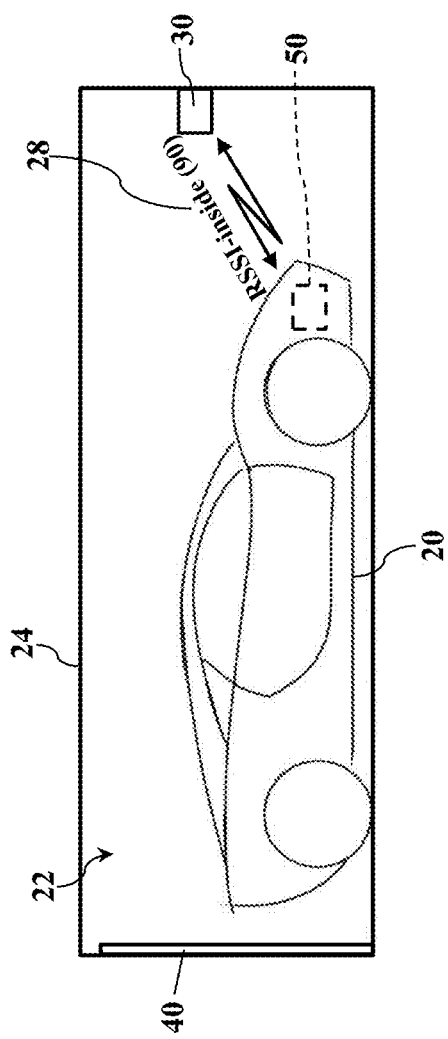
FIGS. 14-15 are schematics further illustrating the locational determination of the vehicle, according to exemplary embodiments.
Figure 15:
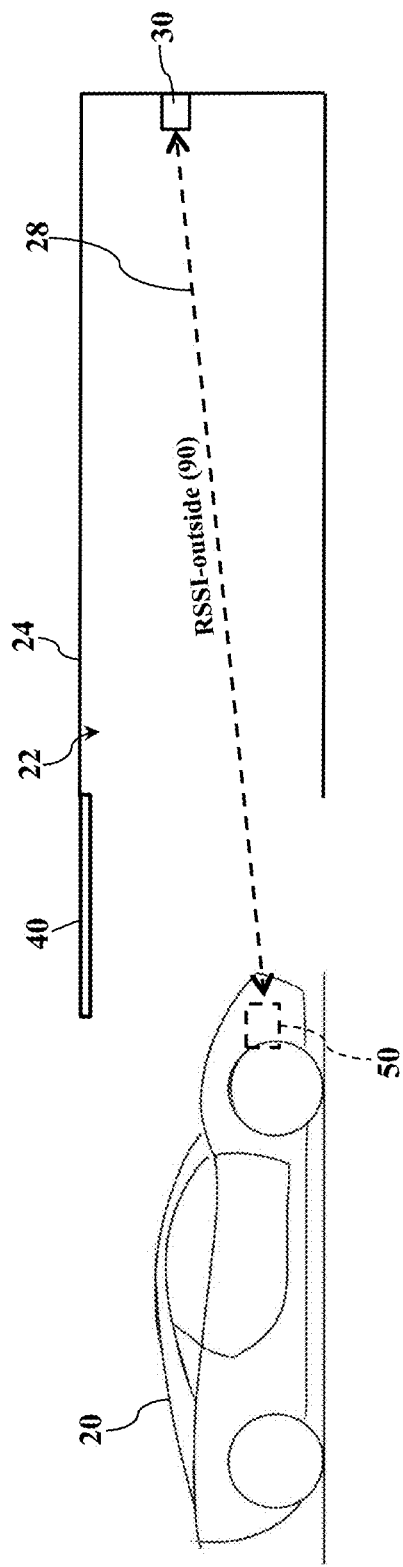

FIGS. 14-15 are schematics further illustrating the locational determination of the vehicle 20, according to exemplary embodiments. As FIG. 14 illustrates, the driver parks the vehicle 20 in the garage 24. Once the vehicle 20 is in the parked position, the vehicle controller 50 may prompt the driver to affirm the parked position. The vehicle controller 50, for example, may generate an audible message that is output by the vehicle's sound system. A graphical message may instead be displayed on the display device (illustrated as reference numeral 102 in FIGS. 6-7). Regardless, the driver may be prompted to make some input confirming the parked position. The vehicle controller 50 may then execute a setup routine that scans for the signal 28 transmitted from the environmental monitor 30. The vehicle controller 50 measures the signal strength 90 and records the measured value (such as "RSSI_inside").

As FIG. 15 illustrates, the driver may also indicate an outside location. Here the driver parks the vehicle 20 outside the garage 24 to ensure clearance of the garage door 40. The vehicle controller 50 then prompts the driver to make another input indicating the vehicle 20 clears the garage door 40. The vehicle controller 50 then again scans for the signal 28 transmitted from the environmental monitor 30. The vehicle controller 50 measures the signal strength 90 and records the measured value (such as "RSSI_outside").

Inferences may then be made. While the vehicle 20 is inside, the measured RSSI value will be higher than RSSI_outside (due to more powerful radio signal) and equal to or lower than RSSI_inside. The vehicle controller 50 thus determines that the vehicle 20 is inside. In this case, the vehicle controller 50 inspects the beacon signal 28 and produces alarms, warnings, and stops the engine 38, if necessary. While the vehicle is outside, the measured RSSI value will be equal to or lower than RSSI_outside. In this case, the vehicle controller 50 determines that the vehicle 20 is outside. When the vehicle 20 is outside, there may not be a need to stop the engine 38, so perhaps only warning messages are displayed.

Figure 16:
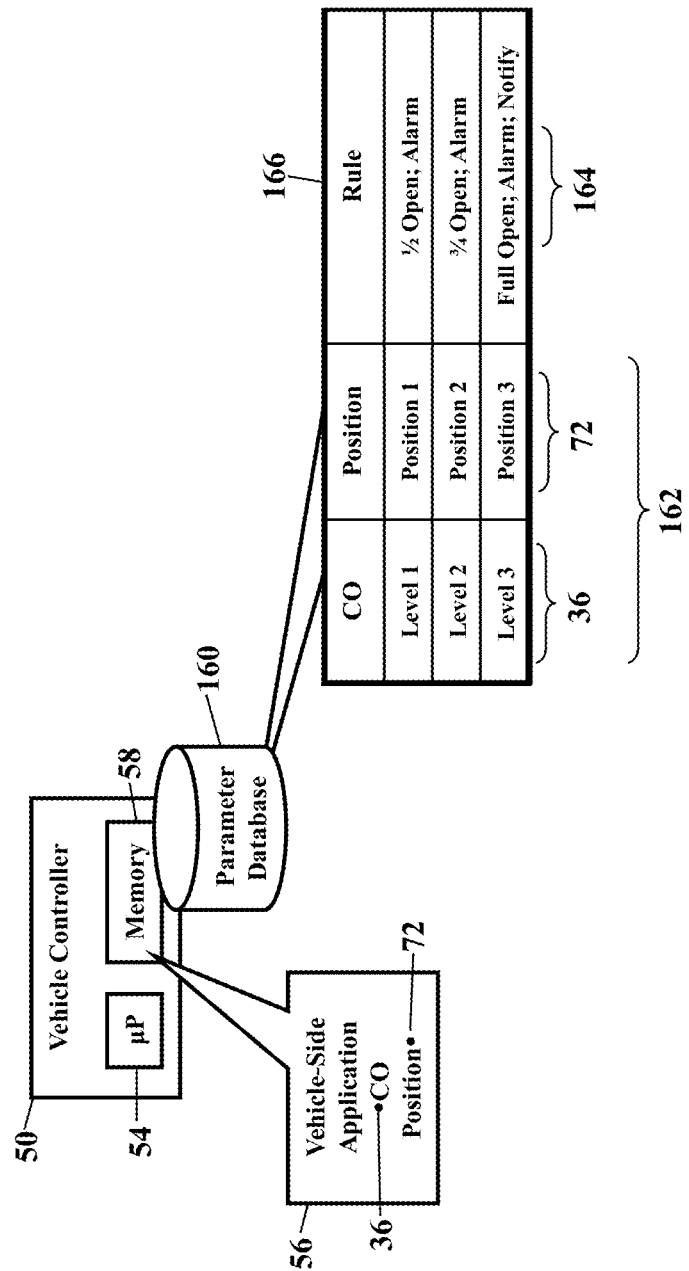
FIGS. 16-17 are schematics illustrating a parameter database, according to exemplary embodiments.
Figure 17:
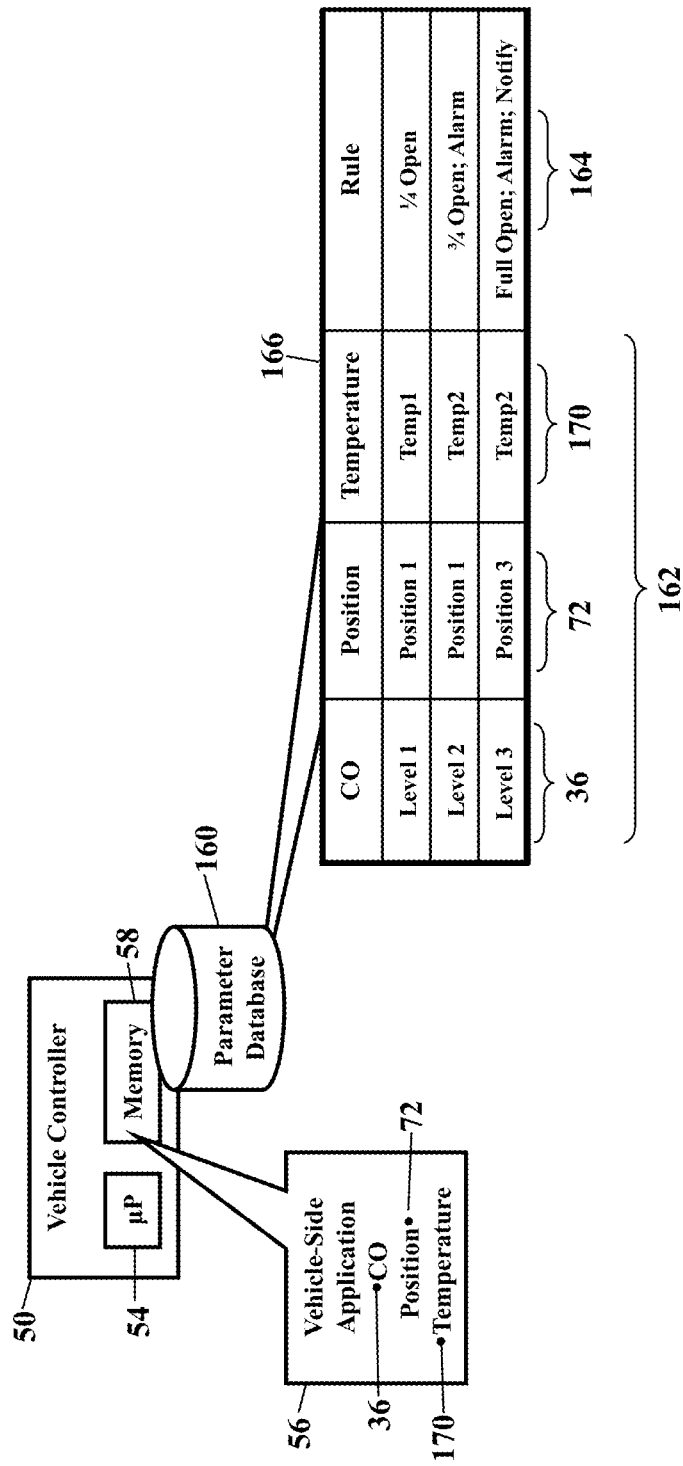

FIGS. 16-17 are schematics illustrating a parameter database 160, according to exemplary embodiments. Here exemplary embodiments may populate entries in the parameter database 160 based on the signals 28 transmitted by the environmental monitor 30. The parameter database 160 may thus associate different parameters 162 to operational rules 164. The parameter database 160 is illustrated as being locally stored in the memory 58 of the vehicle controller 50, but the parameter database 160 may additionally or alternatively be maintained in the environmental monitor 30. The parameter database 160 may even be remotely stored and accessed using the communications network 130. The parameter database 160 is illustrated as a table 166 that maps, relates, or associates the different parameters 162 in the signal 28 to a corresponding rule 164. Once the signal 28 is received, the vehicle controller 50 (and/or the environmental monitor 30) queries the parameter database 160 for the rule 164 associated with the parameters 162. The corresponding rule 164 is retrieved and executed.

FIG. 16 only illustrates a few different rules 164. If the signal 28 indicates that the position 72 of the garage door 40 is "open" and there is no elevated CO parameter 36, then the corresponding rule 164 may require no operation. That is, no harmful carbon monoxide is detected, and the garage door 40 is already open, so ignition is permitted. However, if the position 72 of the garage door 40 is "closed," and the "NOKG" parameter 36 is determined, then the corresponding rule 164 opens the garage door 40. Exemplary embodiments may only partially open the garage door 40 to alleviate the "NOKG" signal 28. That is, rules may be defined that do not require fully opening the garage door 40, especially when the "NOKG" signal 28 is only slightly elevated. Indeed, different levels of carbon monoxide may be associated to different positions 72 of the garage door 40. Smaller levels of carbon monoxide may only require that the garage door 40 be opened to a ¼ position, whereas higher levels may be associated with ¾ or fully open. Even though FIG. 16 only illustrates a few entries in the parameter database 160, in practice the parameter database 160 may have many entries reflecting different environmental conditions and positions.

FIG. 17 adds temperature considerations. Here the environmental monitor 30 may interface with a temperature sensor (not shown for simplicity) to obtain a temperature 170 within the garage 24. When the environmental monitor 30 transmits the signal 28, the signal 28 may thus include information or content describing the temperature 170 within the garage 24. The parameter database 160 may thus further include entries accounting for the temperature 170 within the garage 24. As the reader may understand, any opening of the garage door 40 may have cost penalties, especially in winter months when heating bills may escalate. The rules 164 may thus also be a function of the temperature 170 within the garage 24, such that carbon monoxide is alleviated without excessively opening the garage door 40, thus reducing heating bills.

Exemplary embodiments may consider other sensory factors. For example, a humidity sensor may generate a humidity reading within the garage 24. The garage door 40 may be opened, or closed, based solely on the humidity reading within the garage 24. Similarly, garage door 40 may be opened, or closed, based solely on the temperature 170 within the garage 24. A glass breakage sensor may generate a signal indicating glass has been broken somewhere in the garage 24. Exemplary embodiments may thus disable the vehicle 10 to thwart a thief.

Figure 18:
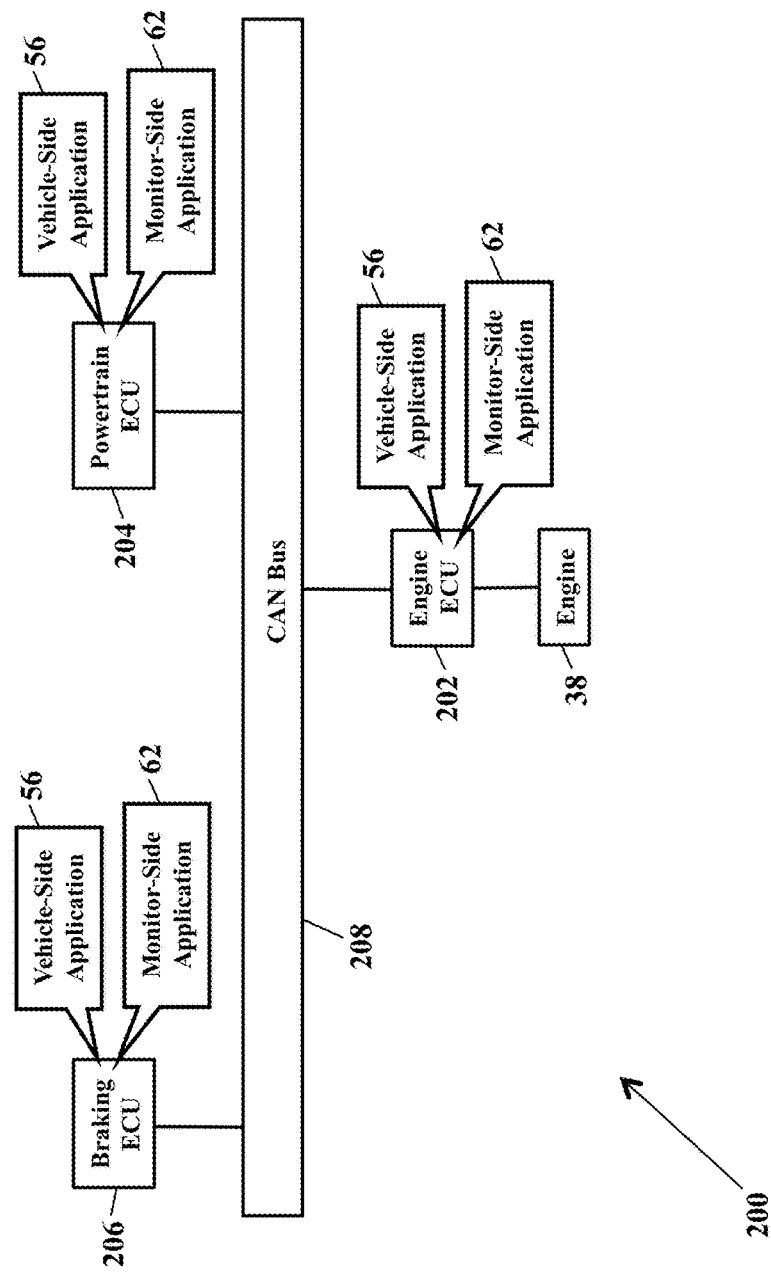
FIG. 18 is a block diagram illustrating a controller area network (or "CAN") 200, according to exemplary embodiments.

FIG. 18 is a block diagram illustrating a controller area network (or "CAN") 200, according to exemplary embodiments. As the reader may understand, the vehicle 10 may have many electronic systems controlling many components and systems. For example, the engine 38 may have an engine controller 202 (or electronic control unit or "ECU"). The transmission may have a powertrain electronic control unit 204. The braking system may have a brake electronic control unit 206. There may be many more electronic control units throughout the vehicle 10. The controller area network 200 thus allows all the various electronic control units to communicate with each other. A CAN bus 208, for example, allows the various electronic control units to send and receive messages that are addressed to one or more of the electronic control units. Any of these controllers may execute some or all of the vehicle-side application 56 and the monitor-side application 62.

Figure 19:
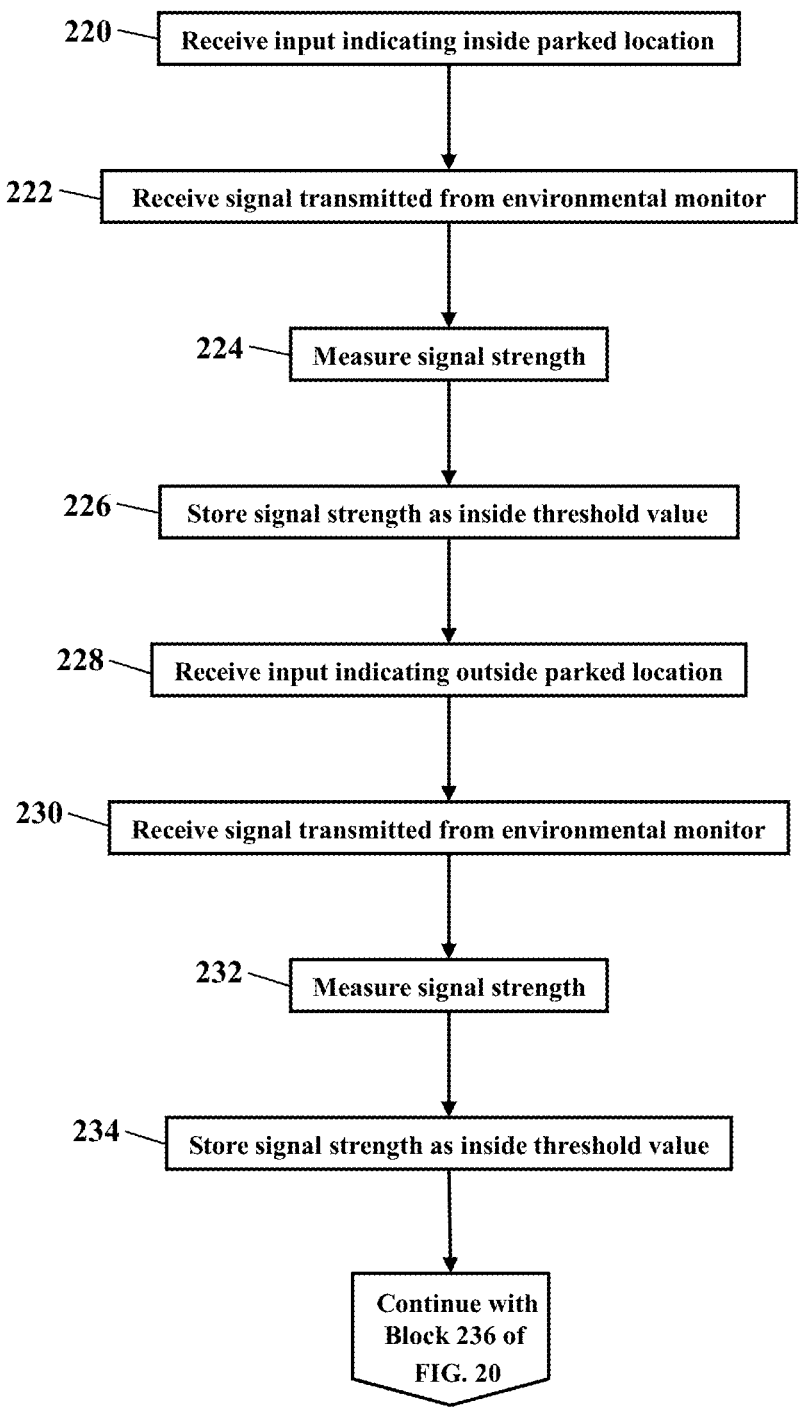
FIGS. 19-20 are flowcharts illustrating an algorithm for monitoring environmental conditions, according to exemplary embodiments.
Figure 20:
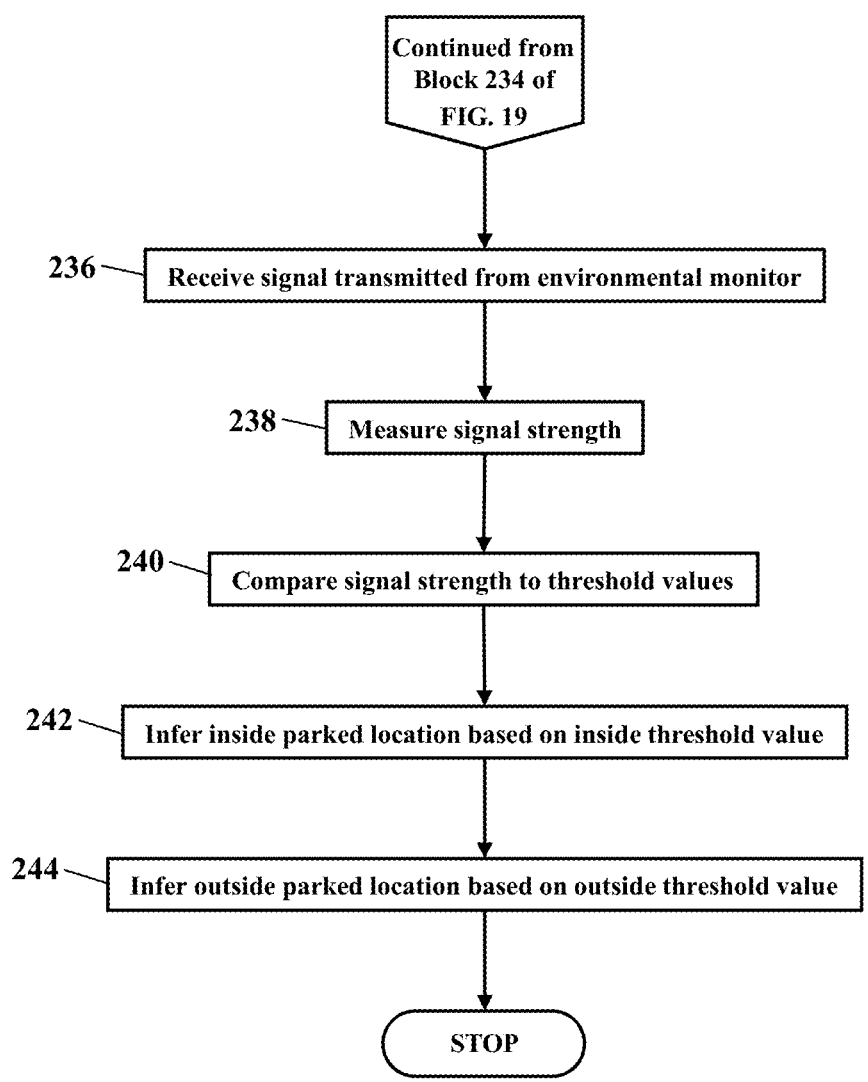

FIGS. 19-20 are flowcharts illustrating an algorithm for monitoring environmental conditions, according to exemplary embodiments. An input is received indicating the vehicle 20 is parked inside the garage (Block 220). The signal 28 is received (Block 222) and its signal strength 90 is measured (Block 224) and stored as an inside threshold value (Block 226). Another input is received indicating the vehicle 20 is parked outside the garage (Block 228). The signal 28 is again received (Block 230) and its signal strength 90 is measured (Block 232) and stored as an outside threshold value (Block 234).

The algorithm continues with FIG. 20. Future signals 28 are received (Block 236) and their signal strengths 90 are measured (Block 238) and compared to the threshold values (Block 240). The inside parked location is inferred based on the comparison to the inside threshold value (Block 242), while the outside parked location is inferred based on the comparison to the outside threshold value (Block 244).

Figure 21:
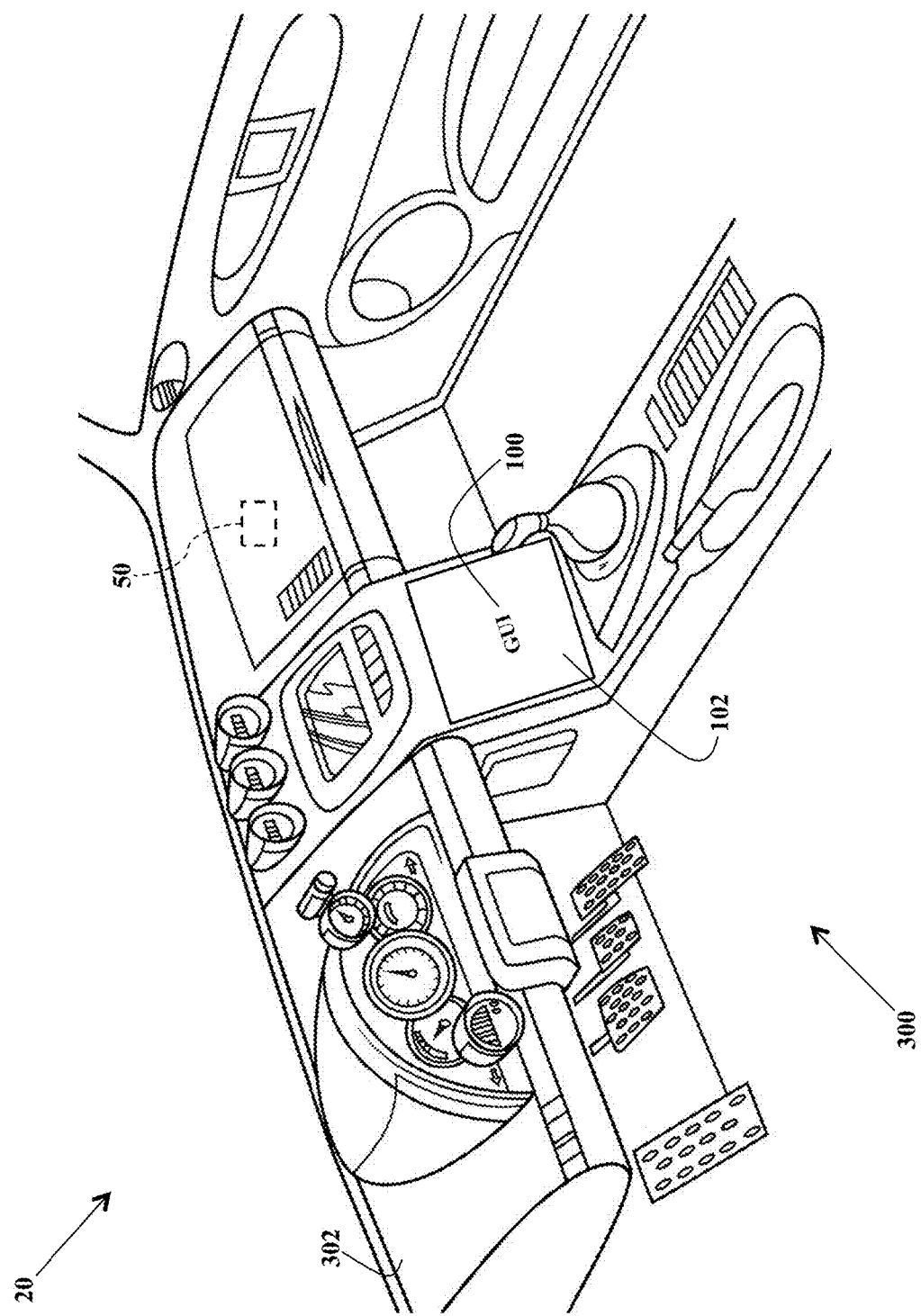
FIGS. 21-23 are schematics further illustrating the operating environment, according to exemplary embodiments.
Figure 22:
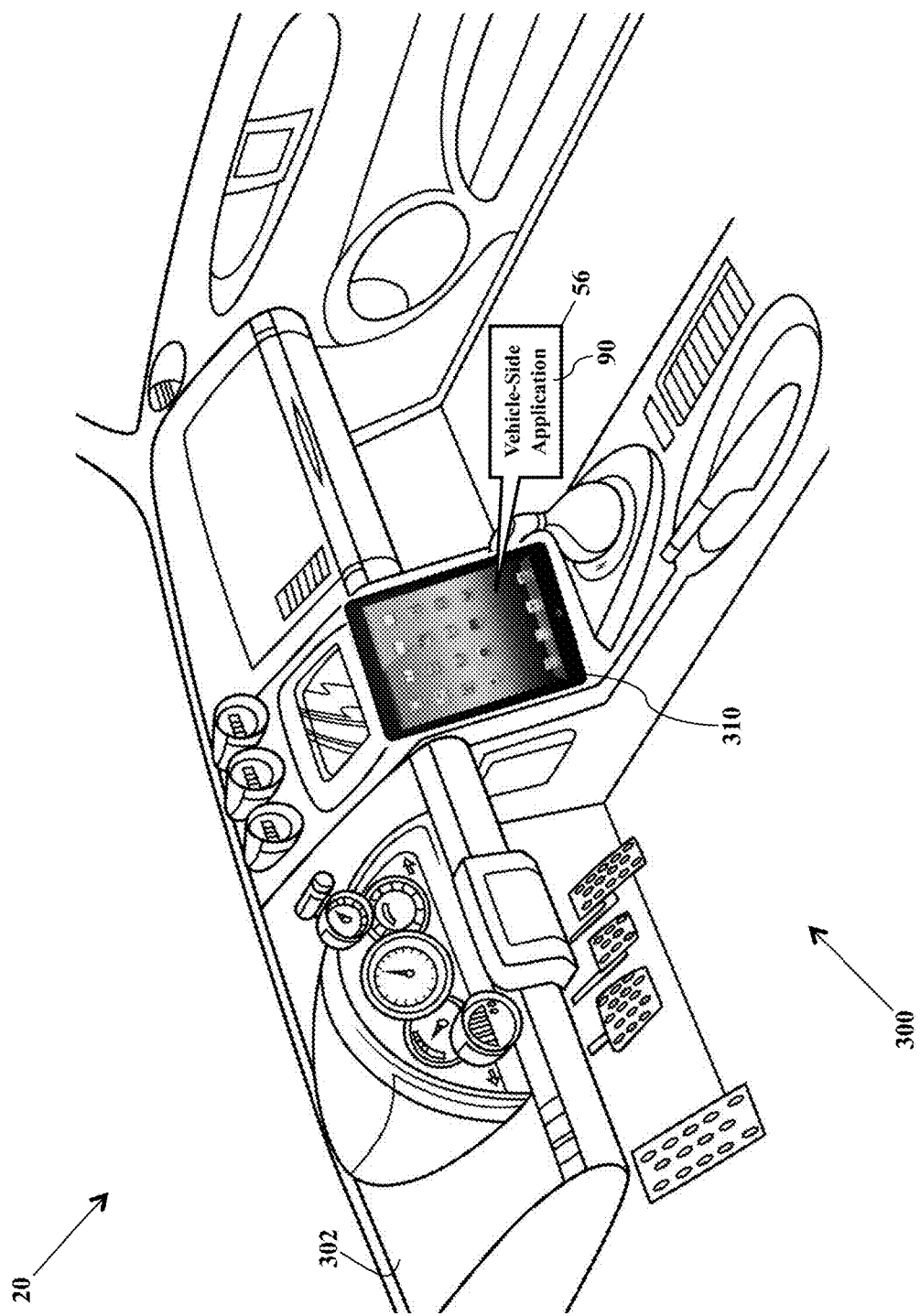
Figure 23:
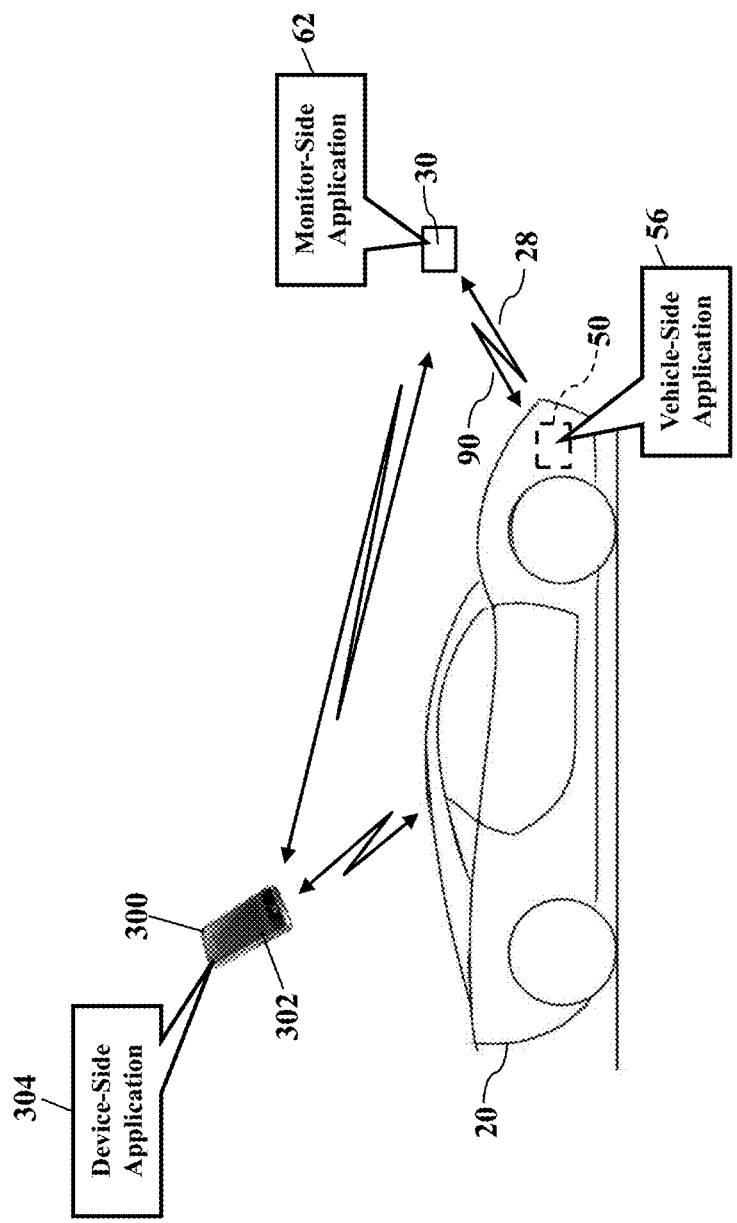

FIGS. 21-23 are schematics further illustrating the operating environment, according to exemplary embodiments. FIG. 21 illustrates the vehicle controller 50 embedded within an automotive interior 300 of the vehicle 20. The automotive interior 300 has many buttons, switches, and other conventional controls for operating the vehicle 20, so the conventional details need not be explained. However, FIG. 21 illustrates an instrument panel 302 into which the display device 102 may be mounted. As the reader may realize, many vehicles have a display for providing touch-based controls and options (such as HVAC, entertainment, navigation, and diagnostic selections). Here, then, the vehicle controller 50 may interface with the display device 102 embedded within or mounted to the instrument panel 302. The vehicle controller 50 generates the graphical user interface 100 for display on the display device 102. The vehicle controller 50 may thus generate prompts and receive inputs, as this disclosure explains.

Exemplary embodiments may thus be a factory offering. As more automotive manufacturers adopt mobile operating systems, some or all of the vehicle-side application 304 may be an "app" that is downloaded to the vehicle 20 for execution. A manufacturer or dealer of the vehicle 20 may thus pre-install the vehicle-side application 304 to help reduce CO exposure. For example, a component supplier may preload the vehicle-side application 304 to some memory component. However, the vehicle-side application 304 may even be retrofitted during a download using an over-the-air network update. That is, a supplier or server downloads the vehicle-side application 304 to the vehicle 20 for execution.

FIG. 22 illustrates a mobile device 310. The mobile device 310 is illustrated as a tablet computer (such as an APPLE® IPAD®), but the mobile device 310 may be any other processor-controlled device (such as a smartphone). Regardless, the mobile device 310 may interface with the vehicle 20 to measure the signal strength 90, as this disclosure explains. FIG. 22, for example, illustrates the mobile device 310 docking with the instrument panel 302. The mobile device 310 may thus interface with the controller area network 200 (illustrated in FIG. 18) to reduce CO emissions, as this disclosure also explains. The mobile device 310, in other words, may download and store some or all of the vehicle-side application 304 to a memory (not shown for simplicity). A processor (also not shown for simplicity) executes the vehicle-side application 304. The mobile device 310 may thus cooperate with the vehicle 20 to measure the signal strength 90 and to determine the location of the vehicle 20, as this disclosure explains.

FIG. 23 also illustrates the mobile device 310. Here, though, the mobile device 310 is illustrated as a smartphone 312, which is enlarged for clarity. The mobile device 310 may interface with the vehicle 20 to receive the signal 28 from the environmental monitor 30. As the reader may understand, mobile devices commonly interface with the vehicle 20 to permit hands-free operation and many other functions. The mobile device 300 may download, store, and/or execute a device-side application 314, which is a set of programming, code, or instructions that cooperate with the vehicle-side application 56 and/or the monitor-side application 62. Should elevated carbon dioxide levels be determined, the mobile device 310 may thus play a role in reducing CO emissions, as this disclosure also explains.

Exemplary embodiments may be physically embodied on or in a computer-readable storage medium. This computer-readable medium may include CD-ROM, DVD, tape, cassette, floppy disk, memory card, USB, and large-capacity disks. This computer-readable medium, or media, could be distributed to end-subscribers, licensees, and assignees. A computer program product comprises processor-executable instructions for monitoring environmental conditions, as the above paragraphs explained.

While the exemplary embodiments have been described with respect to various features, aspects, and embodiments, those skilled and unskilled in the art will recognize the exemplary embodiments are not so limited. Other variations, modifications, and alternative embodiments may be made without departing from the spirit and scope of the exemplary embodiments.

The invention claimed is:

1. A method, comprising:
   receiving, by a controller, a signal generated by an environmental sensor, the signal indicating a carbon monoxide level determined in a garage;
   querying, by the controller, an electronic database for the carbon monoxide level, the electronic database electronically associating positions associated with a door to the garage and carbon monoxide levels including the carbon monoxide level indicated by the signal;
   identifying, by the controller, a position of the positions in the electronic database that is electronically associated with the carbon monoxide level indicated by the signal; and
   generating, by the controller, a command to move the door to the position that is electronically associated with the carbon monoxide level.

2. The method of claim 1, further comprising closing the door.

3. The method of claim 1, further comprising opening the door.

4. The method of claim 1, further comprising determining a signal strength associated with the signal.

5. The method of claim 4, further comprising comparing the signal strength to a threshold value.

6. The method of claim 5, further comprising determining a vehicle is located inside the garage in response to the signal strength.

7. The method of claim 6, further comprising ceasing operation of an engine in the vehicle.

8. A system, comprising:
   a hardware processor; and
   a memory storing instructions that when executed causes the hardware processor to perform operations, the operations comprising:
   receiving a signal generated by an environmental sensor, the signal indicating a carbon monoxide level determined in a garage;
   querying an electronic database for the carbon monoxide level, the electronic database electronically associating positions associated with a door to the garage and carbon monoxide levels including the carbon monoxide level indicated by the signal;
   identifying a position of the positions in the electronic database that is electronically associated with the carbon monoxide level indicated by the signal; and
   generating a command to move the door to the position that is electronically associated with the carbon monoxide level.

9. The system of claim 8, wherein the operations further comprise closing the door.

10. The system of claim 8, wherein the operations further comprise opening the door.

11. The system of claim 8, wherein the operations further comprise determining a signal strength associated with the signal.

12. The system of claim 11, wherein the operations further comprise comparing the signal strength to a threshold value.

13. The system of claim 12, wherein the operations further comprise determining a vehicle is located inside the garage in response to the signal strength.

14. The system of claim 13, wherein the operations further comprise ceasing operation of an engine in the vehicle.

15. A memory device storing instructions that when executed cause a hardware processor to perform operations, the operations comprising:
   receiving a signal transmitted from an environmental sensor, the signal indicating a carbon monoxide level determined in a garage;
   querying an electronic database for the carbon monoxide level, the electronic database electronically associating positions associated with a door to the garage and carbon monoxide levels including the carbon monoxide level indicated by the signal;
   identifying a position of the positions in the electronic database that is electronically associated with the carbon monoxide level indicated by the signal; and
   generating a command to move the door to the position that is electronically associated with the carbon monoxide level.

16. The memory device of claim 15, wherein the operations further comprise determining a signal strength associated with the signal.

17. The memory device of claim 16, wherein the operations further comprise comparing the signal strength to a threshold value.

18. The memory device of claim 16, wherein the operations further comprise ceasing operation of an engine in a vehicle.

19. The memory device of claim 16, wherein the operations further comprise closing the door.

20. The memory device of claim 16, wherein the operations further comprise opening the door.

* * * * *